United States Patent
Liu et al.

(10) Patent No.: US 10,420,711 B2
(45) Date of Patent: *Sep. 24, 2019

(54) DENTAL ADHESIVE WITH POLYMERIZABLE BASIC MONOMERS

(71) Applicant: DENTSPLY SIRONA Inc., York, PA (US)

(72) Inventors: Huaibing Liu, Dover, DE (US); Xiaoming Jin, Middletown, DE (US)

(73) Assignee: DENTSPLY SIRONA Inc., York, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/027,566

(22) Filed: Jul. 5, 2018

(65) Prior Publication Data

US 2018/0325779 A1  Nov. 15, 2018

Related U.S. Application Data

(63) Continuation of application No. 14/507,947, filed on Oct. 7, 2014, now abandoned.

(60) Provisional application No. 61/887,592, filed on Oct. 7, 2013.

(51) Int. Cl.
*A61K 6/00* (2006.01)
*A61K 6/083* (2006.01)

(52) U.S. Cl.
CPC .............. *A61K 6/00* (2013.01); *A61K 6/0023* (2013.01); *A61K 6/083* (2013.01)

(58) Field of Classification Search
None
See application file for complete search history.

(56) References Cited

FOREIGN PATENT DOCUMENTS

DE  102004031524 A1 *  1/2006  ........... A61K 6/0023

* cited by examiner

*Primary Examiner* — Sanza L. McClendon
(74) *Attorney, Agent, or Firm* — Dentsply Sirona Inc.

(57) ABSTRACT

Disclosed herein is a basic dental composition comprising an adhesive composition, wherein the dental composition is suitable for use in dentistry.

1 Claim, No Drawings

DENTAL ADHESIVE WITH POLYMERIZABLE BASIC MONOMERS

TECHNICAL FIELD

A dental composition comprising an adhesive composition, wherein the dental composition is suitable for use in dentistry.

SUMMARY

Disclosed herein is a dental composition comprising an adhesive composition for use in dentistry, wherein the dental composition is basic and therefore mitigates or eliminates residual acid and activation of matrix metallopreteinases that may result from use of an acidic etchant prior to use of the disclosed dental composition.

DETAILED DESCRIPTION

A light-curable dental adhesive composition and kit comprising the adhesive composition for use in restorative dentistry, endodontic, and/or orthodontic applications are disclosed. The disclosed composition is uniquely basic rather than neutral or acidic for a typical dental adhesive.

The disclosed light-curable dental adhesive composition, when used after an acidic etchant, eliminates or at least mitigates the issues caused by the use of the acidic etchant: residual acid and activation of matrix metallopreteinases (MMPs). It is known that any residual acid accelerates resin matrix and collagen degradation, resulting in compromised bond durability. It is also believed that acid activation of MMPs might catalyze collagen degradation, further causing poor long term bond performance.

The disclosed light-curable adhesive composition, when used with a self-etch primer, eliminates or at least mitigates the adverse effect of acidic monomer in the primer on degree of polymerization, enhancing bond strength on tooth substrates.

The disclosed light-curable dental adhesive composition, when used with a self-etch primer, resolves shortcomings associated with current dental adhesives for indirect applications. Common light-cured, acid containing primer or adhesive systems are incompatible with chemical-cured composites to the extent that no effective bonding is achieved for some systems. However, the systems that bonded poorly to the chemically cured composites exhibited high shear bond strengths with the use of light-cured resin composites. Generally, the nature of incompatibility of acid-containing primer or adhesives with chemical-cured resins is attributed to the in situ reaction between the basic component (amine coinitiatior) of the dual-cure restorative and the acid components of the adhesive system. More specifically, these acid components of the bonding agent are able to readily protonate the tertiary aromatic amine, which could be found in the self-curing resin composite as part of the organic redox catalyst. The protonated amine (quaternary aromatic amine) became inactive and/or not reactive towards the peroxide. Consequently, initiating radicals were able to be generated under ambient conditions. Overall, such a catalyst pair would have a loss in efficiency, and the rate and degree of functional group conversion are significantly diminished compromising the performance of the dental adhesive. In order to avoid such an unwanted amine protonation reaction, the dental restoratives to be used in combination have to be limited to those of the photo-curable type only.

The basicity of the disclosed dental adhesive composition is controlled so that the acid from the primer is at least partially neutralized and does not interference with redox initiator systems, especially benzoyl peroxide/tertiary amine redox initiating systems in typical resin cement or core buildup materials. Therefore, when used with self-curing resin cement or core buildup materials, adequate bond strength can be obtained without the use of an additional self-cure activator. The disclosed dental adhesive composition can be used with any acidic dental primer or priming adhesive for any indirect applications.

One embodiment is a kit comprising an acidic primer composition and the disclosed dental adhesive composition that yields significantly increased bond strength on both dentin and enamel.

Another embodiment is a method using the disclosed dental adhesive composition in combination with an acidic primer or priming adhesive to render the primer or priming adhesive for indirect applications and compatible with any self-cured resin cement or composite resin (filing material or core buildup material), indirect restorative procedures (with self-curing resin cement for cementing crowns, bridges and posts).

The disclosed dental adhesive or restorative kit comprises (I) a dental primer composition; and (II) a dental adhesive composition.

The dental adhesive composition comprises:
At least one basic polymerizable monomer having at least one ethylenically unsaturated group,
At least one or more neutral polymerizable monomers having at least one ethylenically unsaturated group,
At least one photoinitiator,
One solvent or mixed solvent, optionally The following formula illustrates the representative structure of basic polymerizable resins. It is expected further alteration from such formulate is possible based on basic knowledge in organic chemistry, which should fall in the scope of this disclosure.

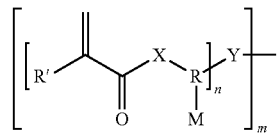

R': H or Me;
X: O, S, NH, NR1 (R1=CH3, C2H5)
R and Y: independently of each other, have C1-C24, linear and/or branched alkylene residue, or aromatic/substituted residue;
M: alpha-substituted tertiary amine, pyridine or substituted pyridine, imidazole and/or substituted imidazole, pyrrole and/or substituted parrole, piperdine and/or substituted piperdine, pyrazole and/or substituted pyrazole, oxazole and/or substituted oxazole, thiazole and/or substituted thiozole, isoxazole and/or substituted isoxazole, isothiazole and/or substituted isoxazole, thiadizole indole and/or substituted thiadizole indole, indolizine and/or substituted indolizine, triazole and/or substituted triazole, tetrazole and/or substituted tetrazole, pentazole and/or substituted pentazole, quinoline and/or substituted quinoline, isoquinoline and/or substituted isoquinoline, pyridazine and/or substituted pyridazine, pyrimidine and/or substituted, pyzazine and/or substituted pyzazine, cinnoline and/or substituted cinnoline, phthalzine pyrimidine and/or substituted phthalzine, quinazoline and/or substituted quinazoline, quinoxaline and/or substituted quinoxaline, phenazine and/or substituted triazines, triazines and/or substituted triazines or any combination of these residues;
n=1-10 and m=1-10.

In the following chart, the typical M is illustrated:

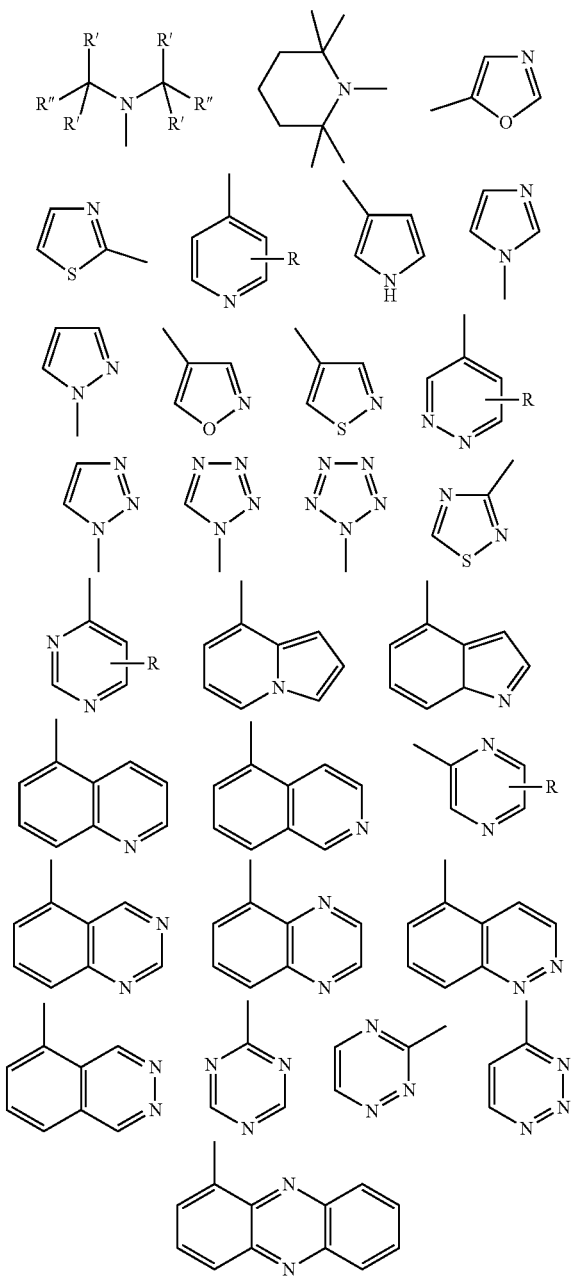

One of representative polymerizable basic resins is polymerizable imidazole resin (IMMA-HEMA) as shown in Scheme 1, which structurally is a dimethacrylate resin containing imidazole moiety. Imidazole is well known for its rather basic property; in fact it is approximately sixty times more basic than pyridine. Thus it should indicate that imidazole intrinsically capable to neutralize readily most of acidic compounds. In addition, unlike other organic basic compounds, such as tertiary amine, imidazole is stable towards oxidants and would not involve in any redox/H-abstraction reactions that occurred in self-cure and/or light-cure process.

Scheme 1: HEMA-based Monoimidazole-dimethacrylate Imidazole Resin (XJ8-48)

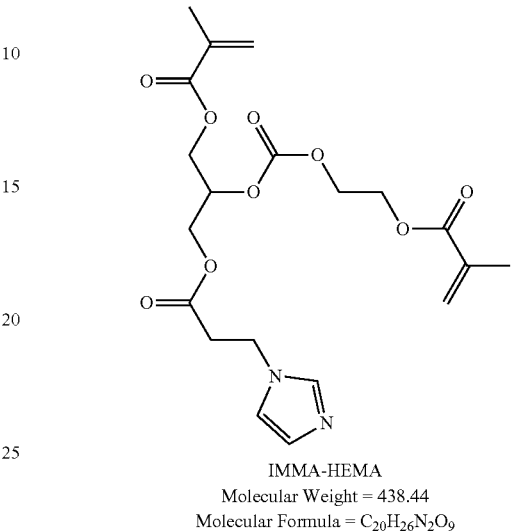

IMMA-HEMA
Molecular Weight = 438.44
Molecular Formula = $C_{20}H_{26}N_2O_9$

For component (ii) of the dental adhesive component, i.e., at least one or more neutral polymerizable monomers having at least one ethylenically unsaturated group, the examples include, but not limited to 2,2-bis[4-(2-hydroxy-3-methacryloylpropoxy)-phenyl]-propane (Bis-GMA), hydroxyethyl methascrylate (HEMA), triethyleneglycol dimethacrylate (TEGDMA), 1,6-Bis[methacryloyloxyethoxycarbonylamino]-2,4,4-trimethylhexane (UDMA).

For component (iii) of the dental adhesive component, i.e., a photoinitiator, the photoinitiator may be any compound that generates free radicals upon exposure to a light source and causes polymerization or hardening of the composition. The light source can be any dental curing light that emits light in the visible or ultraviolet range. Examples of photoinitiators include, but are not limited to, camphorquinone (CQ), 1-phenyl-1,2-propanedione, monoacylphosphine oxide, bisacylphosphine oxide and a mixture of those. A coinitiator may be used with a photoinitiator to enhance curing efficiency. Examples of co-initiators include, but are not limited to, ethyl 4-(N,N-dimethylamino)benzoate (EDAB), 4-(N,N-dimethylamino)benzoic acid, 4-(N,N-dimethylamino)benzonitrile, 4-(N,N-dimethylamino)benzoic acid.

For component (iv) of the dental adhesive composition, i.e., a solvent, the examples include, but not limited to ethanol, water, acetone, methyl ethyl ketone, isopropanol, and t-butanol, or a mixture of two or more of the above.

The resulting dental composition disclosed herein has a basic pH. In embodiments, the dental composition may have a pH of from about 9.6 to about 11.3, such as from about 9.9 to about 11 or from about 10.1 to about 10.8.

Abbreviations for Materials Used in all Examples:
IMMA-HEMA: HEMA-based Monoimidazole-dimethacrylate Imidazole Resin
Bis-GMA: 2,2-bis[4-(2-hydroxy-3-methacryloyl-propoxy)-phenyl]-propane
TEGDMA: triethyleneglycol dimethacrylate CQ: camphorquinome
EDAB: ethyl 4-(N,N-dimethylamino)benzoate
BHT: Butylated hydroxytoluene Comparative Example 1

Bond strength on tooth substrates was evaluated for a commercial all-in-one self-etch adhesive Adper™ Prompt™ L-Pop™ (3M ESPE) to bond TPH®3 composite (Dentsply). The testing procedure is outlined as follows: the extracted human molars were immersed in water and stored in a 4° C. refrigerator prior to use. Dentin or enamel was sanded using wet 320 grit abrasive paper and then 600 grit. The dental adhesive was applied to dentin or enamel surface and. The surface was blown dry with air stream and light cured using Spectrum 800 at 550 mw/cm². For dentin SBS, Gelatin capsules (#5) with diameter of 4.5 mm were half-filled with TPH3 composite and cured in a VL curing oven. The capsules were filled with TPH3 and positioned onto the coated dentin. The flash was gently removed using a dental explorer and the composite was light cured 3×20" sequentially around the circumference of the cylinder with Spectrum 800 at 550 mw/cm². The samples were embedded in tray resin and the posts were ensured to be perpendicular to the bonding surface. After storage in 37° C. water for 24 hr, the shear bond strength was obtained with an Instron at a crosshead speed of 1 mm/min. The similar procedure was followed to test enamel shear bond strength except that plastic straws with diameter of 3.654 mm were used instead of gelatin capsule.

A bond strength of 8.9 (2.0) MPa and 17.6 (2.5) MPa on dentin and enamel respectively was obtained. The low bond strength indicates that most probably Adper™ Prompt™ L-Pop™ is too acidic and as a result the degree of polymerization of the adhesive layer is poor.

Inventive Example 1

Dental Adhesive Composition I
The following were mixed into a homogeneous adhesive composition:
67.96% w/w IMMA-HEMA; 20.60% w/w Bis-GMA; 10.68% w/w TEGDMA; 0.15% w/w CQ; 0.60% w/w EDAB and 0.01% w/w BHT.

The bond strength test in Comparative Example 1 was repeated using Dental Adhesive Composition I in combination with Adper™ Prompt™ L-Pop™ (3M ESPE) to bond TPH®3 composite (Dentsply) as follows: after application of Adper™ Prompt™ L-Pop™, air drying and light curing, one coat of Dental Adhesive Composition I was applied, air dried and light cured. TPH3 composite was placed and light cured. After storage in 37° C. water for 24 hr, the shear bond strength was obtained with an Instron at a crosshead speed of 1 mm/min. A bond strength of 17.7 (3.0) MPa on dentin and 36.9 (8.9) MPa on enamel respectively was obtained. Thus, the increase in bond strength is significant in comparison with the bond strength obtained in Comparative Example 1.

Inventive Example 2

Dental Adhesive Composition II
The following were mixed into a homogeneous adhesive composition:
33.98% w/w IMMA-HEMA; 10.30% w/w Bis-GMA; 5.34% w/w TEGDMA; 0.075% w/w CQ; 0.30% w/w EDAB, 0.005% w/w BHT and 50.00% w/w acetone.

The bond strength test in Comparative Example 1 was repeated using Dental Adhesive Composition II in combination with Adper™ Prompt™ L-Pop™ (3M ESPE) to bond TPH®3 composite (Dentsply) as follows: after application of Adper™ Prompt™ L-Pop™, air drying and light curing, one coat of Dental Adhesive Composition I was applied, air dried and light cured. TPH3 composite was placed and light cured. After storage in 37° C. water for 24 hr, the shear bond strength was obtained with an Instron at a crosshead speed of 1 mm/min. A bond strength of 14.7 (1.4) MPa on dentin was obtained. Thus, the increase in bond strength is significant in comparison with the bond strength obtained in Comparative Example 1.

Comparative Example 2

Bond strength on dentin was evaluated using for a commercial all-in-one self-etch adhesive Adper™ Prompt™ L-Pop™ (3M ESPE) to bond a commercial resin cement Calibra® (Dentsply). The testing procedure is outlined as follows: extracted human molars were wet ground to expose flat surfaces using 320 and 600 grit abrasive paper. Adhesive Adper™ Prompt™ L-Pop™ was applied, air dried and light cured. The plastic straws with diameter 3.654 mm were filled with Calibra and positioned onto the coated dentin or enamel. The flash was gently removed using a dental explorer and the resin cement was let to cure without disturbance for 15 minutes. Bonded specimens were stored in distilled water at 37° C. for 24 hours and embedded in tray resin with posts ensured perpendicular to the bonding surface.

The samples were embedded in tray resin and the posts were ensured to be perpendicular to the bonding surface. After the specimens were stored in 37° C. DI water for 24 hr, the shear bond strength would be obtained in compressive shear mode with an Instron at a crosshead speed of 1 mm/min. However, all testing specimens were debonded automatically during storage in water.

Inventive Example 3

The bond strength test in Comparative Example 1 was repeated using Dental Adhesive Composition I in combination with Adper™ Prompt™ L-Pop™ (3M ESPE) to bond TPH®3 composite (Dentsply) as follows: extracted human molars were wet ground to expose flat surfaces using 320 and 600 grit abrasive paper. Adhesive Adper™ Prompt™ L-Pop™ was applied, air dried. One coat of Dental Adhesive Composition I was applied, air dried and light cured. The plastic straws with diameter 3.654 mm were filled with Calibra and positioned onto the coated dentin or enamel. The flash was gently removed using a dental explorer and the resin cement was let to cure without disturbance for 15 minutes. Bonded specimens were stored in distilled water at 37° C. for 24 hours and embedded in tray resin with posts ensured perpendicular to the bonding surface.

The samples were embedded in tray resin and the posts were ensured to be perpendicular to the bonding surface. After the specimens were stored in 37° C. DI water for 24 hr., the shear bond strength was obtained in compressive shear mode with an Instron at a crosshead speed of 1 mm/min. A bond strength of 10.9 (2.9) MPa on dentin was obtained. Thus, the increase in bond strength is significant in comparison with the bond strength obtained in Comparative Example 2.

The following table summarizes the comparative data results.

|  | Comparative 1 | Inventive 1 | Inventive 2 | Comparative 2 | Inventive 3 |
| --- | --- | --- | --- | --- | --- |
| Dentin SBS in MPa, mean (s.d.) | 8.9 (2.0) | 17.7 (3.0) | 14.7 (1.4) | 0 | 10.9 (2.9) |
| Enamel SBS in MPa, mean (s.d.) | 17.6 (2.5) | 36.9 (8.9) | | | |

We claim:

1. A dental adhesive composition in combination with an acidic primer or priming adhesive to render the acidic primer or priming adhesive for indirect restorative application and compatible with any self-cured resin cement or composite resin, the dental adhesive composition comprising:

- at least one basic polymerizable monomer having at least one ethylenically unsaturated group,
- at least one or more neutral polymerizable monomers having at least one ethylenically unsaturated group,
- at least one photoinitiator,
- and optionally one solvent,
- wherein the dental composition has a pH of from about 9.6 to about 11.3;
- wherein the at least one basic polymerizable monomer having at least one ethylenically unsaturated group has a formula

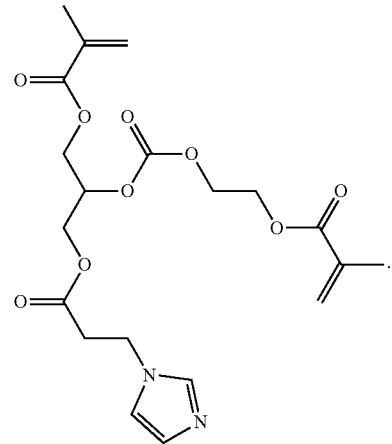 [SMILES: C=C(C)C(=O)OCCOC(=O)OC(COC(=O)CCn1ccnc1)COC(=O)C(=C)C]

* * * * *